United States Patent [19]

Sharma

[11] Patent Number: 5,529,978
[45] Date of Patent: Jun. 25, 1996

[54] N-ACETONYL-SUBSTITUTED-AMIDES

[75] Inventor: Ashok K. Sharma, Horsham, Pa.

[73] Assignee: Rohm and Haas Company, Philadelphia, Pa.

[21] Appl. No.: 237,539

[22] Filed: May 3, 1994

Related U.S. Application Data

[62] Division of Ser. No. 994,247, Dec. 21, 1992, Pat. No. 5,344,978, which is a division of Ser. No. 403,212, Sep. 5, 1989, Pat. No. 5,196,046, which is a division of Ser. No. 634,917, Jul. 26, 1984, Pat. No. 4,863,940.

[51] Int. Cl.$^6$ .......................... A01N 43/42; C07D 215/48
[52] U.S. Cl. .......................... 504/247; 546/139; 546/141; 546/142; 546/145; 546/146; 546/147; 546/148; 546/149; 546/152; 546/153; 546/155; 546/156; 546/157; 546/168; 546/169; 546/172; 546/173; 546/174; 546/175; 546/176; 546/178; 546/179; 546/180
[58] Field of Search .................... 546/139, 141, 546/142, 145 SC, 146, 147–148, 149, 152, 153, 155, 156, 157, 168, 169, 172, 173, 174, 175, 176, 178, 179, 180; 504/247

[56] References Cited

U.S. PATENT DOCUMENTS

| | | |
|---|---|---|
| 3,661,991 | 5/1972 | McNulty et al. |
| 3,751,239 | 8/1973 | McNulty et al. |
| 4,026,902 | 5/1977 | Irikura. |
| 4,163,057 | 7/1979 | Nadelsm. |
| 4,203,994 | 5/1980 | Davenport et al. |
| 4,211,785 | 7/1980 | Nakagawa et al. |
| 4,235,928 | 11/1980 | Eicken et al. |
| 4,328,236 | 5/1982 | Zeeh et al. |
| 4,329,473 | 5/1982 | Almquist et al. |

FOREIGN PATENT DOCUMENTS

| | | |
|---|---|---|
| 37927 | 3/1981 | European Pat. Off. |
| 3247454 | 6/1984 | Germany. |
| 1020761 | 2/1966 | United Kingdom. |

OTHER PUBLICATIONS

Wiegand, et al., CA:112847d, 1969.
Eloy et al., CA:13439x, 1975.
CA107:175901 (EP 224823) (Jun. 10, 1987).
CA105:20509 (EP 170498) (Feb. 5, 1986).
CA94:77864 (US 5344978) (Sep. 6, 1994).
CA93:22333 (US 196046) (Mar. 23, 1993).
CA92:994247 (1992).
CA89:74199 (US 4863940) (Sep. 5, 1989).

*Primary Examiner*—Sharon A. Gibson
*Assistant Examiner*—Catherine Kilby Scalzo
*Attorney, Agent, or Firm*—Joseph F. Leightner

[57] ABSTRACT

Certain N-acetonyl-substituted-amides of the formula:

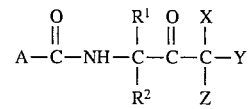

wherein A is a heterocycle, a phenylalkyl, a phenylalkoxy, naphthyl, cycloalkyl, alkoxyalkyl, alkyl, haloalkyl or alkenyl group; X, Y and Z are selected from the group consisting of hydrogen, halo, cyano, thiocyano, isothiocyano, methylsulfonyloxy, thio($C_1$–$C_2$)alkyl, ($C_1$–$C_2$)alkoxy, carbamoyl, dithiocarbamoyl, hydroxy, azide, trifluoromethylcarboxy, ($C_1$–$C_4$)alkylcarbonyloxy, phenylcarbonyloxy, phenoxy, thiophenyl, imidazolyl or triazolyl group as described herein; $R^1$ and $R^2$ are each independently a hydrogen atom or a ($C_1$–$C_6$)alkyl group; and compositions containing these amides are fungicidally active, particularly against phytopathogenic fungi.

7 Claims, No Drawings

N-ACETONYL-SUBSTITUTED-AMIDES

This is a division of Ser. No. 994,247, Dec. 21, 1992, U.S. Pat. No. 5,344,978; which is a division of Ser. No. 403,212, Sep. 5, 1989, U.S. Pat. No. 5,196,046; which is a division of Ser. No. 634,917, Jul. 26, 1984, U.S. Pat. No. 4,863,940.

BACKGROUND OF THE INVENTION

This invention relates to a N-acetonyl-substituted-amide compounds, compositions and methods of controlling fungi, particularly phytopathogenic fungi.

It is known that the benzamides in the class of N-(1,1-dialkyl-3-chloroacetonyl) substituted benzamides have fungicidal activity; see, for example, U.S. Pat. Nos. 3,661,991 and 3,751,239 However, such benzamide compounds, wherein the terminal carbon can only be substituted by chloro or hydrogen atoms, are so phytotoxic that they have no practical use in the treatment of fungal plant infections of plants.

DESCRIPTION OF THE INVENTION

Foliar or soil borne phytopathogenic fungi are controlled by applying a fungicidally effective amount of compounds of formula (I):

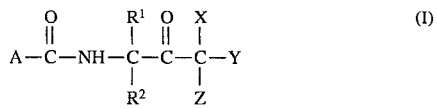

wherein A is a heterocycle selected from furyl, thienyl, isoxazolyl, pyrrolyl, oxazolyl, pyridyl, pyrazolyl, pyrimidinyl, isothiazolyl, thiazolyl, quinolyl and isoquinolyl, phenyl($C_1$–$C_4$)alkyl, cycloalkyl($C_3$–$C_7$), phenyl($C_2$–$C_4$)alkenyl, phenoxy($C_1$–$C_4$)alkyl, naphthyl, the cyclic portions of which may be substituted with up to three, preferably up to two, substituents each independently selected from halo, trifluoromethyl, fluorosulfonyl (—$FSO_2$), methyl, ethyl, methoxy, chloromethyl, ($C_1$–$C_2$)alkoxycarbonyl, cyano, hydroxy or phenyl group; or A is a ($C_1$–$C_8$)alkyl, preferably ($C_1$–$C_6$)alkyl, halo($C_1$–$C_8$)alkyl, preferably halo($C_1$–$C_6$)alkyl wherein the halo is a fluoro, chloro or bromo atom, a ($C_1$–$C_8$)alkoxyalkyl, preferably ($C_1$–$C_6$)alkoxyalkyl or ($C_2$–$C_6$)alkenyl group, preferably a ($C_2$–$C_4$) alkenyl;

X is hydrogen, chloro, bromo, iodo, fluoro, cyano, thiocyano (—SCN), isothiocyano (—NCS), methylsulfonyloxy (—$OSO_2CH_3$), thio($C_1$–$C_2$)alkyl (—SR), ($C_1$–$C_2$)alkoxy (—OR), carbamoyl (—OC(O)$NR^3$), dithiocarbamoyl (—SC(S)$NR^3$), hydroxy (—OH), azide (—$N_3$), ($C_1$–$C_4$)alkycarbonyloxy (—OC(O)R), phenylcarbonyloxy (—OC(O)∅) trifluoromethylcarbonyloxy ($CF_3$COO—), phenoxy, phenylthio, imidazolyl and triazolyl group;

Y and Z are each independently a hydrogen, bromo, chloro, iodo, fluoro, cyano, thiocyano (—SCN), isothiocyano, (—NCS), methylsulfonyloxy (—$OSO_2CH_3$), thio($C_1$–$C_2$)alkyl (—SR), ($C_1$–$C_2$)alkoxy (—OR), carbamoyl (—OC(O) $NR^3$), hydroxy (—OH), azide (—$N_3$), or ($C_1$–$C_4$)alkylcarbonyloxy (—OC(O)R) group and either Y or Z may be an imidazolyl or triazolyl group;

each R is independently an alkyl group;

$R^1$ and $R^2$ are each independently a ($C_1$–$C_6$)alkyl group;

each $R^3$ in a molecule is independently a hydrogen or a ($C_1$–$C_4$)alkyl group, preferably a hydrogen or a ($C_1$–$C_2$)alkyl group.

When X contains a phenylcarbonyloxy, phenoxy or phenylthio substituent, the phenyl moiety may be substituted with one substituent selected from the group consisting of chloro, fluoro, bromo, iodo or methyl group.

Preferred compounds of the invention are ones wherein A is furyl, phenylthio, isoxazolyl, oxazolyl, pyridyl, phenoxy($C_1$–$C_4$)alkyl, phenyl($C_2$–$C_4$)alkenyl, trichloromethyl or trifluoromethyl and when A is a cyclic substituent, its cyclic portion may be substituted with up to three, preferably up to two, substituents selected from chloro, bromo, fluoro, ($C_1$–$C_4$)alkyl or phenyl group;

$R^1$ and $R^2$ are each independently a ($C_1$–$C_4$)alkyl group;

X is hydrogen, chloro, bromo, iodo, methylsulfonyloxy, thio($C_1$–$C_2$)alkyl, isothiocyano (—NCS) or thiocyano (—SCN) group;

Y is a hydrogen, bromo, chloro, cyano or iodo atom; and

Z is a hydrogen, chloro or bromo atom.

More preferred compounds of the invention are ones wherein A is isoxazolyl, phenylisoxazolyl, phenoxy($C_1$–$C_2$)alkyl or pyridyl wherein the cyclic portion of each of these substituents is substituted with up to two substituents independently selected from chloro and bromo atoms; $R^1$ and $R^2$ are each independently ($C_1$–$C_2$)alkyls; X is a bromo, iodo, methylsulfonyloxy, isothiocyano or thiocyano group; Y is a hydrogen, bromo, chloro or iodo atom; and Z is a hydrogen atom. Most preferably, $R^1$ is a methyl group; $R^2$ is an ethyl group; X is a bromo atom; Y is a hydrogen, bromo, iodo or chloro atom; and Z is a hydrogen atom.

Typical compounds of the invention include:

N-(1',1'-Dimethyl-3',3'-dibromoacetonyl)-thiophen-2-carboxamide

N-(1',1'-Dimethyl-3',3'-dibromoacetonyl)-isonicotinamide

N-(1',1'-Dimethyl-3',3'-dibromoacetonyl)-nicotinamide

N-(1',1'-Dimethyl-3',3'-dibromoacetonyl)-5-chloronicotinamide

N-(1',1'-Dimethyl-3',3'-dibromoacetonyl)-6-methylnicotinamide

N-(1',1'-Dimethyl-3'-bromo-3'-chloroacetonyl)-hexan-1-oic amide

N-(1'-Bromo-1'-chloro-3'-methylpentan-2'-on-3'-yl)-2-naphthoic amide

N-(1'-Bromo-1'-chloro-3'-methylpentan-2'-on-3'-yl)-picolinic amide

N-(1'-Bromo-1'-chloro-3'-methylpentan-2'-on-3'-yl)-5-chlorofuran-2-carboxamide

N-(1'-Bromo-1'-fluoro-3'-methylpentan-2'-on-3'-yl)-2-phenyloxazol-5-carboxamide

N-(1',1'-Dibromo-3'-methylpentan-2'-on-3'-yl)-pyrimidin-5-carboxamide

N-(1'-Bromo-3'-methylhexan-2'-on-3'-yl)-cyclohex-2-en-1-carboxamide

N-(3'-Methyl-1'-cyanoheptan-2'-on-3'-yl)-pyrazol-1-carboxamide

N-(1'-Acetyl-3'-ethylpentan-2'-on-3'-yl)-3-chlorophenoxyacetamide

N-(1',1'-Dimethyl-3'-thiocyancacetonyl)-4-chlorobutyramide

N-(3'-Methyl-1'-ethylthiopentan-2'-on-3'-yl)-pyrrol-1-carboxamide

N-(3'-Methyl-1'-methylsulfonytoxypentan-2'-on-3'-yl)-isoquinolin-3-carboxamide

N-(1',1'-Dimethyl-3'-azidoacetonyl)-hex-2-en-1-oic amide

N-(1'-Imidazolyl-3'-methylhexan-2'-on-3'-yl)-diphenylacetamide

N-(3',3'-Dibromo-1',1'-dimethyiacetonyl)-2,4-dichlorocinnamic amide

Preferred compounds include:

N-(1'-Thiocyano-3'-methylpentan-1'-on-3'-yl)-6-chloronicotinamide

N-(1'-Bromo-3'-methylpentan-2'-on-3'-yl)-5,6-dichloronicotinamide

N-(1',1'-Dibromo-3'-methylpentan-2'-on-3'-yl)-2,6-dichloroisonicotinamide

N-(1'-Bromo-1'-chloropentan-2'-on-3'-yl)-6-chloronicotinamide

N-(1'-Bromo-1'-chloro-3'-methylpentan-2'-on-3'-yl)-quinolin-3-carboxamide

N-(3'-Bromo-3'-chloro-1',1'-dimethylacetonyl)-4-chloro-2-naphthoic amide

N-(1'-Bromo-1'-chloro-3'-methyl-2'-oxopentan-3-yl)-2,4-dichloro-cinnamic amide. and more preferred compounds include:

N-(1',1'-Dibromo-3'-methylpentan-2'-on-3'-yl)-4-fluoro-2-naphthoic amide

N-(1'-Bromo-1'-fluoro-3'-methylpentan-2'-on-3'-yl)-6-chloro-5-methylnicotinamide N-(3'-Bromo-3'-chloro-1',1'-dimethylacetonyl)-2,6-dimethylisonicotinamide N-(3'-Methyl-1'-thiocyanopentan-2'-on-3'-yl)quinolin-3-carboxamide N-(1'-Bromo-3'-methylpentan-2'-on-3'-yl)-2,4,6-trichlorophenoxyacetamide.

The compounds of the present invention provide a means for controlling phytopathogenic Phycomycetes and some fungi classified as Deuteromycetes (Fungi Imperfecti), Ascomycetes, and Basidiomycetes. Important genera of the Phycomycetes include Phytophthora, Plasmopora, Peronospora, and Pseudoperonospora which cause diseases such as potato and tomato late blight, and downy mildews in grapes, squash, melons, broccoli and other cole crops. Basidiomycetes, such as Pellicularia and Puccinia spp. are also controlled by the invention. Species of these genera cause diseases such as rice sheath blight (*Pelllcularia filamentosa*) and rusts, e.g., *Puccinia graminis* and *Puccinia recondita*. Plant root and stalk rots caused by Fusarium spp. can also be controlled by the present invention.

Late blights, downy mildews, many root rots and damping-off diseases have been difficult to control due to the lack of effective control methods. Some of the more effective chemical control measures have become ineffective due to the development of resistant fungal strains. The compounds of Formula (I) can be used to control these types of fungi, particularly late blights and downy mildews.

The amides of the invention can be applied as fungicidal sprays by methods commonly employed, such as conventional high-gallonage hydraulic sprays, low-gallonage sprays, air-blast, aerial sprays and dusts. The dilution and rate of application will depend upon the type of equipment employed, the method and frequency of application desired and diseases to be controlled, but the effective amount is usually from about 0.5 kilogram (kg) to about 20 kg, preferably from about 1 to about 5 kg of active ingredient per hectare.

As a seed protectant, the amount of toxicant coated on the seed is usually at a dosage rate of about 1 kg to about 5 kg and preferably from about 0.5 to about 2.5 kg per 100 kilograms of seed. As a soil fungicide the chemical dan be incorporated in the soil or applied to the surface usually at a rate of 0.5 to about 20 kg and preferably about 1 to about 5 kg per hectare. As a foliar fungicide, the amides are usually applied to growing plants at a rate of about 0.5 to about 5 and preferably from about 1 to about 2.5 kg per hectare.

The present invention is useful for the control of fungi and can be utilized at various loci such as the seed, the soil or the foliage. For such purposes these compounds can be used in the technical or pure form as prepaired, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in *McCutcheon's Emulsifiers* and *Detergents, McCutcheon's Emulsifiers* and *Detergents/Functional Materials* and *McCutcheon's Functional Materials* all published annually by McCutcheon Division of MC Publishing Company (New Jersey).

In general, the compounds of this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5 to 50%.

For the preparation of emulsifiable concentrates, the compounds used in the invention can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of N-(3'-Bromo-3'-chloro-1',1'-dimethylacetonyl)nicotinamide, 45 parts of a synthetic precipitated hydrated silicon dioxide sold under the trademark Hi-Sil® and 5 parts of sodium lignosulfonate (Marasperse® N-22). In another preparation of a kaolin type (Barden) clay is used in place of the Hi-Sil in the above wettable powder and in another such preparation 25% of the Hi-Sil is replaced with a synthetic sodium silico aluminate sold under the trademark Zeolex® 7.

Dusts are prepared by mixing the amides and salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing 20% to 80% of the active ingredient are commonly made and are subsequently diluted to 1% to 10% use concentration.

The amides used in the invention can be readily prepared using conventional synthesis techniques. For example, compounds of Formula (I) can be prepared in accordance with Schemes I and II.

Scheme I

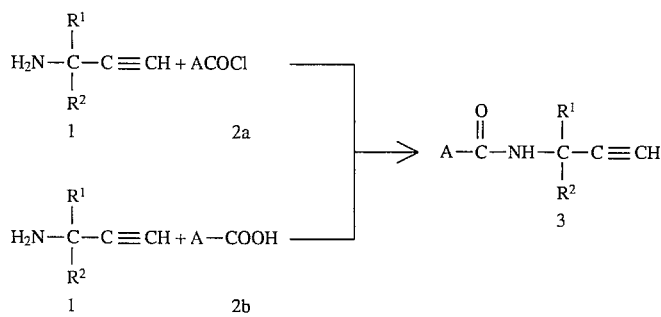

The starting materials, N-propynylamides (3), are prepared by reacting the commercially available acid chlorides (2a) with propynylamines (1) in solvents, such as water, methylene chloride, ether, tetrahydrofuran (THF), dioxan, glyme, toluene and hexane, at temperatures ranging from about 0° to about 100° C. and preferably at about 0° to 20° C. A base is used to neutralize the hydrochloric acid produced in the reaction. Generally sodium hydroxide, pyridine, triethylamine, 2,6-lutidine, dimethylaminopyridine, N-methylmorpholine or another such base is used.

Alternatively, compounds of structure (3) may also be prepared by activating the acid (2b) with a reagent such as isobutylchloroformate, trifluoroacetic anhydride, methanesulfonylchloride, dicyclohexylcarbodiimide, 1-methyl-2-chloropyridinium iodide, diethylazodicarboxytate, N,N-dimethylphosphoramidic dichloride, and then reacting it with the amine (1). Use of these reagents in such reactions has been described in the literature.

The halogenated ketones of structure (6a), (6b) and (6c) are available via the chemistry shown in Scheme II.

Scheme II

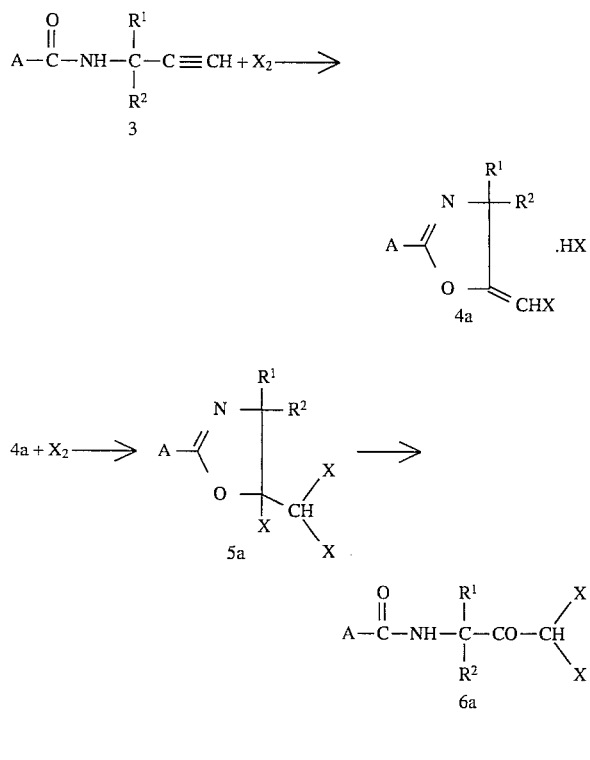

-continued
Scheme II

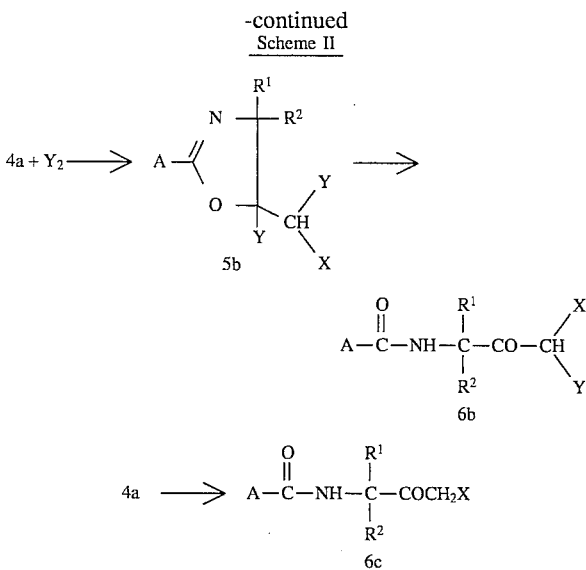

The propynyl amide (3) is treated with one equivalent of chlorine, bromine, or another halogenating agent ($X_2$) such as N-chlorosuccinimide, N-bromosuccinimide, sodium hypochlorite, pyridinium hydrobromide perbromide, to afford the oxazoline structure (4a) as a hydrohalide salt which can be easily converted to its free base by standard methods such as treatment with pyridine, triethylamine, aqueous sodium carbonate, sodium hydroxide or another similar base. This oxazoline (4a) as a free base may be then reacted with another halogenating agent or halogen ($Y_2$) as described above to obtain oxazolines (5a) or (5b). Hydrolysis of these oxazolines readily provides the products (6a) and (6b) in which the product has either two identical halogens (6a) or two different halogens (6b). Hydrolysis can be carried out in solvents like THF, dimethoxyethane, dioxane, alcohols, dimethylsulfoxide, dimethylformamide, along with the aid of aqueous mineral acids, such as hydrochloric and sulfuric acid, at temperatures in the range of about 20° to about 80° C. and preferably at about 20° to 50° C. When only one halogen is desired as in product (6c), the oxazoline (4a) is hydrolyzed under conditions described above to obtain product (6c).

In those cases where "X" in structure (6c) is other than halogen, these groups may be introduced by a nucleophilic substitution of X. Such substitutions can be successfully accomplished using alkali metal (such as lithium, sodium or potassium) salts of cyanide (—CN), thiocyanate (—SCN), dithiocarbamate [—SC(—S)NR$_2$], 1,2,4-triazole, imidazole, azide, sulfide (—SR) or acetate [—OC(—O)R] in solvents such as toluene, acetone, glyme, dimethylformamide and dimethylsulfoxide; and at temperatures ranging from about 20° C. to about 100° C. Procedures for carrying out these transformations are well known in the chemical literature. Catalysis of these reactions using crown ethers is also well known.

The compounds of the present invention can also be utilized in combination with other fungicides such as:

(a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (proplneb), sodium methyldithiocarbamate (metham), tetramethylthiuram disulfide (thiram), the complex of zineb and polyethylene thiuram disulfide, 3,5-dimethyl-1,3,5-2H-tetrathydrothiadiazlne-2-thione (dazomet); and mixtures of these and mixtures with copper salts;

(b) nitrophenol derivatives such as: dinitro-(1-methylheptyl) phenyl crotonate (dinocap), 2-sec -butyl-4,6-dinitrophenyl-3,3-dimethylacrylate (binapacryl), and 2-sec-butyl-4,6-dinitrophenyl isopropyl carbonate;

(c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazolone-3, 2,4-dichloro-6-(o-chloroanilino)-s-triazine, diethyl phthalimido-phosphorothloate, 4-butyl-1,2,-triazole, 5-amino-1-[bis(dimethylamino)phosphinyl]-3-phenyl-1,2,4-trizaole, 5-ethoxy-3-trichloromethyl-1,2,4-thiadiazole, 2,3-dicyano-1,4-dithiaanthraquinone (dithianon), 1,3-dithiolo-[4,5-b]quinoxaline-2-thione (thioquinox), methyl 1-(butylcarbamoyl)-2-benzimidazole carbamate (benomyl), 2-4'-(thiazolyl) benzimidazole (thiabendazole), 4-(2-chlorophenylhydrazono)-3-methyl-5-isoxazolone, 3-(3,5-dichlorophenyl)-5-ethenyl-5-methyl-2,4-oxazolidinedione (vinclozolin); 3-(3, 5-dichlorophenyl)-N-(1-methylethyl)-2,4-dioxo-1-imidazolidinecarboxamide (iprodione); N-(3,5-dichlorophenyl)-1,2-dimethylcyclopropane-1,2-dicarboximide (procymidone); beta-(4-chlorophenoxy)-alpha-(1,1-dimethylethyyl)-1H-1,2,4-triazole-1-ethanol (triadimenol); 1-(4-chlorophenoxy)-3,3-dimethyl-1-(1H-1, 2,4-triazol-1-yl)-2-butanone (triadimefon); beta-[(1,1'-biphenyl)-4-yloxy]-alpha-(1,1 -dimethylethyl)-1H -1,2,4-triazole-1-ethanol (bitertanol); 2,3-dichloro-N-(4-fluorophenyl) malelmide (fluoroimide); 1-[2-(2,4-dichlorophenyl)-4 -propyl-1,3-dioxolan-2-ylmethyl]-1H-1,2,4-triazole; pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, alpha-(phenyl)-alpha-(2,4-dichlorophenyl)-5-pyrimidinyl-methanol (triarimol), cis-N-[(1,1,2,2-tetrachloroethyl)thio]-4-cyclohexene-1,2-dicarboximide, 3-[2-(3,5-dimethyl-2-oxycyclohexyl-2-hydroxy]-glutarimide (cycloheximide), dehydroacetic acid, N-(1,1,2,2-tetrachloroethylthio) -3a, 4,7,7a-tetrahydrophthalimide (captafol), 5-butyl-2-ethylamino-4-hydroxy -6-methyl-pyrimidine (ethirimol), acetate of 4-cyclodecyl-2,6-dimethyl-morpholine (dodemorph), and 6-methyl-2-oxo-1,3-dithiolo[4,5-b]-quinoxaline (quinomethionate).

(d) miscellaneous halogenated fungicides such as: tetrachloro-p-benzoquinone (chloranil), 2-3-dichloro-1,4-napthoquinone (dichlone), 1,4-dichloro-2,5-dimethoxybenzene (chloroneb), 3,5,6-trichloro-o-anisic acid (tricamba), 2,4,5, 6-tetrachloroisophthalonitril (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as:
griseofulvin, kasugamycin and streptomycin;

(f) copper-based fungicides such as: copper hydroxide, cuprous oxide, basic cupric chloride, basic copper carbonate, copper terphthalate, copper naphthenate and Bordeaux mixture; and (g) miscellaneous fungicides such as: diphenyl, sultone, dodecylguanidine acetate (dodine), phenylmercuric acetate, N-ethyl-mercuri-1,2,3,6-retrahydro-3,6-endomethano-3,4,5, 6,7,7-hexachlorophthalimide, phenyl-mercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, 1,2-bis (3,-methoxycarbonyl-2-thioureido) benzene (thiophanate-methyl).

It is particularly advantageous to utilize the present invention in combination with a dithiocarbamate, e.g., mancozeb or maneb for added control of non-Phycomycetes fungi.

EXAMPLES

The following compounds listed in Table 1 are meant to be illustrative of the invention.

TABLE 1

$$A-\underset{\|}{C}-NH-\underset{\underset{CH_3}{|}}{\overset{CH_3}{\underset{|}{C}}}-\underset{\|}{C}-\underset{\underset{Z}{|}}{\overset{X}{\underset{|}{C}}}-Y$$

| Example | A | X | Y | Z | Elemental Analysis Calculated (Found) or NMR |
|---------|---|---|---|---|----------------------------------------------|
| 1 | [structure: isoxazole with φ and CH₃ substituents] | Br | Br | H | $^1$H-NMR: 7.8, br, 5H; 6.6, S, 1H; 6.3, br, 1H; 2.7, S, 3H; 1.45, S, 6H |
| 2 | [structure: Br-phenyl-OCH₂-] | Br | Br | H | $^1$H-NMR: 6.8–7.6, ABq, 4H; 7.2, br, 1H; 6.6, S, 1H; 4.5, S, 2H; 1.7, S, 6H. Anal. for C$_{13}$H$_{14}$NO$_3$Br$_3$: Calc'd. (Found): C=33.99(34.95), H=3.05(3.19), N=3.05(3.15). |

TABLE 1-continued $$A-\overset{O}{\underset{\|}{C}}-NH-\overset{CH_3}{\underset{CH_3}{\overset{|}{C}}}-\overset{O}{\underset{\|}{C}}-\overset{X}{\underset{Z}{\overset{|}{C}}}-Y$$

| Example | A | X | Y | Z | Elemental Analysis Calculated (Found) or NMR |
|---------|---|---|---|---|---|
| 3 | 2-furyl | Br | Br | H | ¹H-NMR: CDCl₃, 7.5, d, 1H; 7.15, m, 1H; 6.6, dd, 1H; 7.4, br, 1H; 6.6, S, 1H; 1.8, S, 6H. Anal. for C₁₀H₁₁Br₂No₃: Calc'd. (Found): C=33.90(34.34), H=3.11(3.17), N=3.95(3.92), Br=45.19(43.38). |
| 4 | 2-thienyl | Cl | H | H | ¹H-NMR: CDCl₃, 8.5, br, 1H; 7.95, m, 1H; 7.65, m, 1H; 7.15, m, 1H; 4.5, S, 2H; 1.6, S, 6H. |
| 5 | 3,4,5-trichloro-2-furyl | Br | Br | H | ¹H-NMR: CDCl₃, 6.95, br, 1H; 6.6, S, 1H; 1.8, S, 6H. |
| 6 | 2-thienyl | Br | Br | H | ¹H-NMR: CDCl₃, 9.5, br, 1H; 8.0, m, 1H; 7.8, m, 1H; 7.2, m, 1H; 1.8, S, 6H. Anal. for C₁₀H₁₁Br₂NSO₂: Calc'd. (Found): C=32.52(32.27), H=2.98(3.05), N=3.79(3.70), S=8.67(8.67), Br=43.36(41.98). |
| 7 | 4-pyridyl | Br | Br | H | ¹H-NMR: CDCl₃, 9.0–8.5 and 7.8, several m, 5H; 6.7, S, 1H; 1.7, S, 6H. Anal. for C₁₁H₁₂Br₂N₂O₂: Calc'd. (Found): C=36.29(35.88), H=3.32(3.43), N=7.69(7.41), Br=43.90(43.15). |
| 8 | 2,6-dichloro-4-pyridyl | Br | Br | H | ¹H-NMR: CDCl₃, 9.0, br, 1H; 8.0, S, 2H; 6.65, S, 1H; 1.8, S, 6H. Anal. for C₁₁H₁₀Br₂Cl₂N₂O₂: Calc'd. (Found): C=30.52(30.51), H=2.33(2.28), N=6.47(6.42), Br=36.91(35.63), Cl=16.38(16.72). |
| 9 | 2-naphthyl | Br | Br | H | ¹H-NMR: CDCl₃, 8.5–7.5, several m, 8H; 6.7, S, 1H; 1.8, S, 6H. Anal. for C₁₄H₁₅Br₂NO₂: Calc'd. (Found): C=46.52(46.79), H=3.66(3.71), Br=38.68(35.41), N=3.39(3.30). |
| 10 | 1-(2,4-dichlorophenoxy)ethyl | Br | Br | H | ¹H-NMR: CDCl₃, 7.6, m, 1H, 7.2, br, 1H; 7.0, m, 1H; 6.45, S, 1H; 4.7, Q, J=8 Hz, 1H; 1.75, S, 6H; 1.73, d, J=8 Hz, 3H. Anal. for C₁₄H₁₄Br₂Cl₃NO₃: Calc'd. (Found): C=32.94(32.65), H=2.76(2.86), N=2.74(2.75), Cl=20.84(21.89), Br=31.31(28.97). |
| 11 | 2-chloro-4-pyridyl | Br | Br | H | ¹H-NMR: CDCL₃, 8.8, m, 1H; 8.2–8.0, m, 1H; 7.50, m, 1H; 7.4, br, 1H; 6.6, S, 1H; 1.75, S, 6H. Anal. for C₁₁H₁₁Br₂ClN₂O₂: Calc'd. (Found): C=33.16(32.41), H=2.78(2.88), N=7.03(6.78); Br=40.10(41.23), Cl=8.90(8.46), O=8.03(8.11). |

TABLE 1-continued

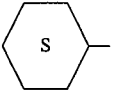

| Example | A | X | Y | Z | Elemental Analysis Calculated (Found) or NMR |
|---|---|---|---|---|---|
| 12 | [thiophene ring, S]— | Cl | H | H | $^1$H-NMR: (CDCl$_3$) 7.0, br, 1H; 4.5, S, 2H; 1.8, S, 6H; 0.8–2.2, m, 11H. |
| 13 | CH$_3$(CH$_2$)$_3$— | Br | Br | H | $^1$H-NMR: CDCl$_3$, 7.4, br, 1H; 6.6, S, 1H; 2.3–2.6, m, 2H; 1.7, S, 6H; 0.9–2.0, several m, 7H. Anal. for C$_{10}$H$_{17}$NO$_2$Br$_2$: Calc'd. (Found): C=34.99(34.42), H=4.96(4.92), N=4.08(4.07), Br=46.65(45.94). |
| 14 | Cl$_3$C— | Br | Br | H | $^1$H-NMR: CDCl$_3$, 7.5, br, 1H; 6.5, S, 1H; 1.8, S, 6H. |

EXAMPLE 3

N-(1',1'-Dimethyl-3',3'-dibromoacetonyl)-furan-2-carboxamide a) N-(1',1'-Dimethylpropynl)-furan-2-carboxamide 2-Furoyl chloride (6.5 gm, 0.05 m) was dissolved in methylene chloride. (200 ml), cooled to 0° to −5° C. and maintained under a nitrogen atmosphere. Triethylamine (10 ml) and then dimethylpropargylamine (4.2 gm, 0.051 m) were gradually added with stirring while maintaining the temperature at 0±5° C. for about one-half hour and then at room temperature for about 1 hour. Water (100 ml) was added and the reaction slurry was transferred, using methylene chloride ( 100 ml) as a rinse, to a separatory funnel. The aqueous layer was sequentially separated and the methylene chloride layer was washed with water 50 ml), 5% hydrochloric acid (1×100 ml) , saturated sodium bicarbonate (1×50 ml), water (1×50 ml) and then brine. The solvent was evaporated after drying over magnesium sulfate and 8.0 gms of product were obtained. The starting materials for all compounds except 7, 8 and 11 can be prepared in an analogous manner.

b) N-(1',1'-Dimethyl -3',3'-dibromoacetonyl)-furan-2-carboxamide

N-(1',1'-dimethylpropynyl)-furan-2-carboxamide (3.04 gm, 0.02 m) was dissolved in methylene chloride (50 ml) and placed in a 100 ml round bottom flask equipped with a magnetic stirrer, heating mantle and a reflux condenser. Bromine (6.4 gm, 0.04 m) was added and the mixture was heated to reflux for about one-half hour. The reaction mixture was cooled, diluted with hexane and the resulting yellow precipitate was filtered. The precipitate was dissolved in methanol (30 ml), water (10 ml) was added and the solution heated to and maintained at about 50° C. for 8 hours. After cooling to room temperature and subsequent dilution with water, a white solid formed which was collected by filtration and dried. Recrystallization from a mixture of chloroform and hexane gave 3.0 gm of pure product.

Compounds of examples 1, 2, 5–10 and 13 and 14 were analogously prepared.

EXAMPLE 4

N-(3'-Chloro-1',1'-dimethylacetonyl) thiophen-2-carboxamide

N-( 1',1'-dimethylpropynyl)thiophen-2-carboxamide (1.5 gm, 0.0078 mole) in hexane (50 ml) was placed in a round bottom flask equipped with magnetic stirrer and an addition funnel. Chlorine (0.6 gm, 0.0084 m) in ethyl acetate (10 ml) was added with stirring and stirred for about another 2 hours. Then hexane (50 ml) was added and the white solid obtained was collected by filtration. This solid was taken with methanol (50 ml), water (10 ml) and hydrochloric acid (5 ml) and the resulting mixture heated to about 50° C. for about one hour. The reaction solution was poured into ice water (200 ml) and the white solid formed was collected by filtration. The crude product was chromatographed on silica using ethylacetate and hexane (20:80) to obtain 800 mg of product.

EXAMPLE 11

(a)

N-(1',1'-Dimethylpropynyl)-6-chloronicotinamide

A 500 ml three neck flask was equipped with a mechanical stirrer, a thermometer, addition funnel, a gas inlet and a cooling bath. 6-Chloronicotinic acid (15.0 gm, 0.095 mole) along with dry THF (150 ml) was placed in this flask and was cooled to about −20° C. under a nitrogen atmosphere. Triethylamine (9.8 gm, 0.10 mole) was added in one portion, followed by the dropwise addition of methanesulfonyl chloride (11.4 gm, 0.01 mole) while maintaining the reaction mixture at −10° to −20° C. Upon complete addition of methanesulfonyl chloride, the mixture was stirred at about −20° C. for one hour. 1,1-Dimethylpropargyl amine (11.9 gm, 0.14 mole) was added gradually while keeping the reaction mixture below −10° C., then was stirred at this temperature for 1 hour. The resulting product was processed in a manner analogous to that described in example 3a. Recrystallization of the crude product from a mixture of hexane and methylene chloride (95:5) afforded 19 gm pure product.

The starting materials for examples 7 and 8 were prepared analogously.

(b) N-(3',3'-Dibromo-1',1'-dimethylacetonyl)-6-chloronicotamide was prepared from N-(1',1'-dimethylpropynyl)-6-chloronicotinamide in a manner analogous to the procedure described in step (b) of Example 3. The compounds of examples 7 and 8 were also prepared using a procedure analogous to that described for example 3, step (b).

EXAMPLE 12

N-(3'-chloro-1',1'-dimethylacetonyl) cyclohexancarboxamide

N(1',1'-dimethylpropynyl)cyclohexancarboxamide (2.0 gms., 0.0104 m) was dissolved in hexane (30 ml) and chlorine gas was bubbled through it at room temperature until 0.8 gm was absorbed. The resulting white precipitate was filtered, taken in methanol (30 ml), water (10 ml) and concentrated hydrochloric acid (5 ml) and heated to 40°–50° C. for about one hour. The reaction was poured into ice water and white solid formed was filtered and dried. This solid was a mixture of two products from which the desired product was separated by column chromatography.

EXAMPLE 15

The compounds of examples 1–14 were tested for their fungicidal activity. The compounds were tested in vivo against cucumber downy mildew (*Pseudoperonospora cubensis*) and tomato late blight (*Phytophthora infestaris*) and in vitro against *Pythium ultimum* and *Phytophthora capsici*.

a) Cucumber Downy Mildew (CDM)

*Pseudoperonospora cubensis* was maintained on leaves of live cucumber plants in a constant temperature room at 65° to 75° F. in humid air with moderate light intensity for 7 to 8 days. A water suspension of the spores from infested leaves was obtained and the spore concentration was adjusted to about $1\times10^5$ spores per milliliter (ml).

Marketer cucumber seedlings were selected at the one to two true leaf stage and thinned to one plant (or two leaves) per pot. The seedlings were sprayed to run-off with a solution of a test compound comprising 300 ppm of the active ingredient of the test compound in a 2:1:1 mixture of water, acetone and methanol. After drying, a spore suspension of cucumber downy mildew was applied to the lower surface of the plant leaves with a DeVilbiss atomizer until fine droplets were visible on the leaves. The inoculated seedlings were placed in a humidity cabinet for 24 hours at 65° to 75° F. and then placed into an intermittent mist chamber which is located in the controlled temperature room. (The mist chamber provided 85–90% relative humidity and temperature of the room was constantly 68° F. at 1000 footcandle (f.c.) of light intensity on a 12 hour diuranal cycle.) Treatment evaluations were made 7 to 8 days after inoculation. The results are reported in Table 2 as the percent disease control and represents the level of disease suppression when compared to the untreated plants.

b) Grape Downy Mildew (GDM)

Five to six inch DeChaunac grape plants in three-inch pots were selected for use in the test. The plants were sprayed with the solution of the compound (described in 15(a)) using a three nozzle mechanical sprayer and allowed to dry four to six hours. One set of plants (untreated) were not sprayed with any of the compounds.

Grape downy mildew (*Plasmopora viticola*) inoculum was prepared by washing conidia from sporulating leaves. The spore suspension was standardized to a concentration of about $4\times10^5$ spores/ml and hand sprayed onto the underside of the leaves with a DeVilbiss atomizer. The plants were inoculated for 24 hours in a humidity cabinet at 20° C. and subsequently moved to a constant temperature room of 20° C. and 1000 f.c. of light on a 12 hour cycle. After six days the plants were placed in a mist chamber for 24 hours at 20° C. after which sporulation was apparent on the underside of the leaves. Treatment evaluations were then made. The results are reported in Table 2 as percent disease control which represents the percentage of the treated plants lacking disease signs or symptoms when compared to untreated control plants.

c) Tomato Late Blight (TLB)

*Phytophthora infestans* was maintained on 6 to 8 inch tall Rutgers tomato seedlings for 4 to 5 days in a constant temperature humidity chamber at 65° to 75° F. with moderate light intensity. A water suspension of the spores from infested plants was obtained and the spore concentration was adjusted to about $1\times10^5$ spores per ml.

Rutgers tomato seedlings, 3 to 5 inches tall, were fertilized with a water-soluble fertilizer to promote rapid succulent growth. About 4 to 5 days later, the seedlings were sprayed to run-off with a solution of a test compound comprising 300 ppm of the active ingredient of the test compound in a 2:1:1 mixture of water, acetone and methanol. After drying, the tomato late blight spore suspension was applied to the lower leaf surface with a DeVilbiss atomizer until fine droplets were visible on the leaves. The incolulated seedlings were placed in a humidity cabinet at 65° to 70° F. for 24 hours and then moved to a humidity controlled temperature chamber until treatment evaluations were made 5 to 7 days after inoculation. The results are reported in Table 2 as percent disease control which represents the percentage of the treated plants (leaves and stems) lacking disease signs or symptoms when compared to untreated control plants.

d) In Vitro Tests

In Vitro testing was done to determine the effects of the test compounds on the mycelial growth of *Pythium ultimum* and *Phytophthora capsici*. Corn meal agar was autoclaved for 15 minutes and agar suspensions containing a concentration of each test compound at 100 ppm (volume to weight basis). The agar was poured into petri dishes and allowed to harden. Thereafter, 6 mm, circular mycelial fungal plugs of 1 week old stock cultures grown on amended corn meal agar were placed on the surface of the agar in the petri dishes. The dishes were incubated under light at room temperature, about 22° C., for 2 days (*P. ultimum*) and three days (*P. capsici*) until the colonies in the control dishes had grown about half or more of the diameter of the petri dish. The control dishes consisted of corn meal agar amended with 2 ml of acetone and the solvent used for the test compounds. The diameter (mm) of the mycelial growth in each dish was measured. The results are reported in Table 2 as percent growth inhibition calculated from the measured colony diameters of the control colonies and colonies grown in the presence of test compounds as follows:

$$\text{Percent Growth Inhibition} = \frac{\text{Dia. of Control Growth (mm)} - \text{Dia. of Test Cpd. Growth (mm)}}{\text{Diameter Control Growth (mm)}} \times 100$$

TABLE 2

| Example | In Vivo (300 ppm) | | | In Vitro (100 ppm) | |
|---|---|---|---|---|---|
| | CDM | GDM | TLB | P. ultimum | P. capsici |
| 1 | 100 | 100 | 100 | 88 | 100 |
| 2 | 50 | 100 | 100 | 100 | 100 |
| 3 | 80 | 100 | 20 | 100 | 100 |
| 4 | 0 | 100 | 20 | 100 | 74 |
| 5 | 90 | 100 | 80 | 93 | 100 |
| 6 | 20 | 100 | 50 | 100 | 100 |
| 7 | 70 | —* | 0 | 100 | 100 |
| 8 | 80 | 100 | 30 | 100 | 100 |
| 9 | 80 | 100 | 40 | 39 | 57 |
| 10 | 20 | 100 | 90 | 68 | 78 |
| 11 | 40 | —* | 0 | 100 | 100 |
| 12 | 10 | 60 | 0 | 4 | 30 |
| 13 | 80 | 100 | 100 | 93 | 100 |
| 14 | 0 | —* | 10 | 100 | 100 |

*not tested.

What is claimed is:

1. A compound of the structure

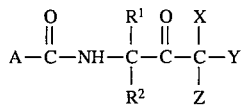

wherein

1) A is selected from the group consisting of quinolyl and isoquinolyl; either of which may be substituted with up to three substituents independently selected from the group consisting of halo, trifluoromethyl, fluorosulfonyl, methyl, ethyl, methoxy and phenyl;

2) X is selected from the group consisting of hydrogen, chloro, bromo, iodo, fluoro, cyano, thiocyano, isothiocyano, methylsulfonyloxy, thio($C_1$–$C_2$)alkyl, ($C_1$–$C_2$)alkoxy, carbamoyl (—OC(O)NR$^3$), dithiocarbamoyl (—SC(S)NR$^3$), hydroxy, azide, ($C_1$–$C_4$)alkylcarbonyloxy, phenylcarbonyloxy, trifluoromethylcarbonyloxy, phenoxy, phenylthio, imidazolyl and triazolyl, when X is a phenylcarbonyloxy, phenoxy or phenylthio substituent, the phenyl moiety is substituted with up to one substituent selected from chloro, fluoro, bromo, iodo or methyl group; and 3) Y and Z are each independently selected from the group consisting of a hydrogen, bromo, chloro, iodo, fluoro, cyano, thiocyano, isothiocyano, methylsulfonyloxy, thio ($C_1$–$C_2$)alkyl, ($C_1$–$C_2$)alkoxy, carbamoyl (—OC(O)NR$^3$), hydroxy, azide or ($C_1$–$C_4$)alkylcarbonyloxy group and either Y or Z may be an imidazolyl or triazolyl group;

4) R$^1$ and R$^2$ are each independently selected from the group consisting of hydrogen and (C-$_1$–$C_6$)alkyl group; and each R$^3$ in a molecule is independently selected from hydrogen and a ($C_1$–$C_4$)alkyl group.

2. The compound N-(3'-methyl-1'-thiocyanopentan-2'-on-3'-yl)quinolin-3-carboxamide.

3. A fungicidal composition comprising a fungicidally effective amount of the compound of claim 1 and an agronomically acceptable carrier.

4. A method for controlling phytopathogenic fungi comprising applying to a plant, to plant seed or to plant habitat a fungicidally effective amount of the compound of claim 1.

5. The method of claim 4 wherein the compound is applied in an amount of from about 0.5 to about 20 kilograms per hectare.

6. The method of claim 5 wherein the compound is applied in an amount of from about 1 to about 5 kilograms per hectare.

7. The compound N-(1'-bromo-1'-chloro-3'methylpentan-2'-on-3'-yl)-quinolin-3 -carboxamide.

* * * * *